US008655717B2

(12) United States Patent
Schwarzberg et al.

(10) Patent No.: US 8,655,717 B2
(45) Date of Patent: Feb. 18, 2014

(54) SYSTEM AND METHOD FOR REWARDING USERS FOR CHANGES IN HEALTH BEHAVIORS

(75) Inventors: Robert Schwarzberg, Boca Raton, FL (US); Marion Zabinski, Boca Raton, FL (US); Renee Melton, Delray Beach, FL (US); Timothy J. Dion, Parkland, FL (US)

(73) Assignee: Humana Innovations Enterprises, Inc., Louisville, KY (US)

( * ) Notice: Subject to any disclaimer, the term of this patent is extended or adjusted under 35 U.S.C. 154(b) by 1227 days.

(21) Appl. No.: 11/856,917

(22) Filed: Sep. 18, 2007

(65) Prior Publication Data

US 2009/0076903 A1 Mar. 19, 2009

(51) Int. Cl.
*G06Q 10/00* (2012.01)
(52) U.S. Cl.
USPC ............ 705/14; 705/2; 705/14.1; 705/14.58; 705/14.67
(58) Field of Classification Search
USPC ............................... 705/2, 14.1, 14.58, 14.67
See application file for complete search history.

(56) References Cited

U.S. PATENT DOCUMENTS

| | | | |
|---|---|---|---|
| 5,377,258 A | 12/1994 | Bro | |
| 5,673,691 A | 10/1997 | Abrams et al. | |
| 5,832,448 A | 11/1998 | Brown | |
| 5,890,128 A | 3/1999 | Diaz et al. | |
| 5,897,493 A | 4/1999 | Brown | |
| 5,954,510 A | 9/1999 | Merrill et al. | |
| 6,039,688 A | 3/2000 | Douglas et al. | |
| 6,246,992 B1 | 6/2001 | Brown | |
| 6,366,871 B1 | 4/2002 | Geva | |
| 6,602,191 B2 | 8/2003 | Quy | |
| 6,811,516 B1 | 11/2004 | Dugan | |

(Continued)

FOREIGN PATENT DOCUMENTS

| | | |
|---|---|---|
| WO | 9944494 | 9/1999 |
| WO | 2006021956 | 3/2006 |
| WO | 2006138680 | 12/2006 |

OTHER PUBLICATIONS

Be Well Mobile, A Picture of Health, Patient Engagement Software That Works, http://www.bewellmobile.com; http://www.bewellmobile.com/products-services.html; http://www.bewellmobile.com/biographies.html; http://www.bewellmobile.com/patient-engagement.html, 6 pages from website, Copyright 2006, Feb. 21, 2007.

(Continued)

*Primary Examiner* — Naresh Vig
(74) *Attorney, Agent, or Firm* — Standley Law Group LLP

(57) ABSTRACT

A system and method for generating and sending reward messages to users accomplishing goals related to a personalized health behavior plan. Rewards may be issued for reasons such as achieving an ultimate goal, reaching an intermediate goal, or completing a suggested activity such as eating a suggested meal or performing a suggested physical activity. A reward may be a coupon for use at an establishment such as a restaurant, a clothing store, or a fitness center. Rewards may also be checks sent through postal mail or coupons for printing on a personal printer. Reward messages are generated by an expert system based on a user's personalized diet, exercise, or other health plan, goals associated with the plan, and specified preferences. Reward messages are sent to user's portable devices. Current location information may be used to send a user a reward for use at a nearby establishment.

20 Claims, 18 Drawing Sheets

(56) References Cited

U.S. PATENT DOCUMENTS

| | | | |
|---|---|---|---|
| 6,936,007 | B2 | 8/2005 | Quy |
| 6,968,375 | B1 | 11/2005 | Brown |
| 6,976,958 | B2 | 12/2005 | Quy |
| 7,090,638 | B2 | 8/2006 | Vidgen |
| 7,156,809 | B2 | 1/2007 | Quy |
| 7,222,054 | B2 | 5/2007 | Geva |
| 7,361,141 | B2 * | 4/2008 | Nissila et al. .............. 600/300 |
| 7,668,832 | B2 | 2/2010 | Yeh et al. |
| 2002/0065713 | A1 * | 5/2002 | Awada et al. ................ 705/14 |
| 2002/0128804 | A1 | 9/2002 | Geva |
| 2005/0021361 | A1 | 1/2005 | Huang et al. |
| 2005/0021372 | A1 | 1/2005 | Mikkelsen et al. |
| 2005/0049920 | A1 * | 3/2005 | Day et al. .................... 705/15 |
| 2005/0113649 | A1 | 5/2005 | Bergantino |
| 2005/0113650 | A1 * | 5/2005 | Pacione et al. ............. 600/300 |
| 2005/0234742 | A1 * | 10/2005 | Hodgdon ........................ 705/2 |
| 2006/0041452 | A1 | 2/2006 | Kulkarni |
| 2006/0058586 | A1 | 3/2006 | Humble |
| 2006/0064447 | A1 | 3/2006 | Malkov |
| 2006/0178907 | A1 | 8/2006 | Humble |
| 2006/0189853 | A1 | 8/2006 | Brown |
| 2006/0199155 | A1 | 9/2006 | Mosher |
| 2006/0287883 | A1 | 12/2006 | Turgiss et al. |
| 2007/0021984 | A1 | 1/2007 | Brown |
| 2007/0030339 | A1 | 2/2007 | Findlay et al. |
| 2011/0307311 | A1 * | 12/2011 | Turgiss et al. ............. 705/14.4 |

OTHER PUBLICATIONS

BeWell Mobile Forms Partnership with Wipro for Disease Management, BeWell Also Named Finalist in Global Software Competition Conduct by Qualcomm, Press Release, Dec. 6, 2006.

Diet Tiny Assist, http://www.wimos.com/diet.html, 4 pages from website, Feb. 16, 2007.

Welcome to Health Hero Network, Making Connections for Life, Heath Buddy System, http://www.healthhero.com/products services/products services.html; http://www.healthhero.com/products services/peripherals.html, 4 pages from website, Copyright 2006, Feb. 12, 2007.

Palm OS, Keyoe, Software products to organize and enhance your life, http://www.keyoe.com/DEA Handheld.htm, 8 pages from website, Copyright 2000-2007, Last modified: Dec. 2, 2006, Feb. 16, 2007.

Card Guard AG and Humana form new company to provide innovative wireless platform for wellness and disease management, Press Release, Oct. 17, 2005.

Ali, Sarmad, Technology Enlisting cellphones to fight cellulite, The Wall Street Journal, http://www.post-gazette.com/pg/06236/716009-96.stm, Aug. 24, 2006.

Sensei, Changing Mindsets with Handsets, http://www.sensei.com, 1 page from website, Copyright 2005, Mar. 13, 2007.

Card Guard: Card Guard receives approval from Israeli Court to become Swiss-based, Press Release, 1 page from website, Oct. 23, 2001, http://www.cardguard.com/newsite/inner.asp?lang=1&newsid=43&type=1&cat=44.

* cited by examiner

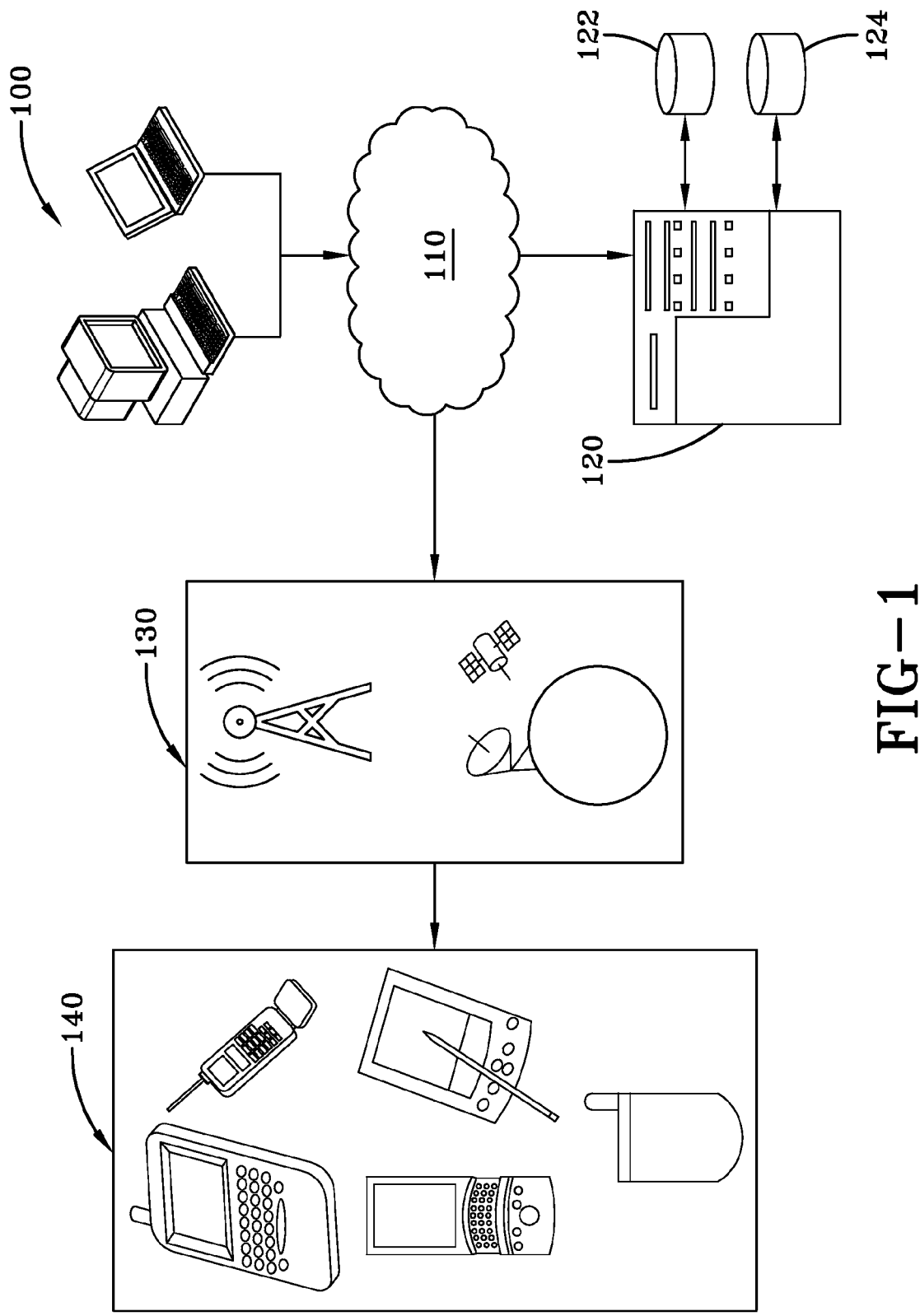

HOME · WHY Sensei · ARTICLES · RECIPES · HEALTH TOOLS · FAQ · About Sensei · JOIN          MY Sensei.com (login)

*Sensei*  CHANGING MINDSETS WITH HANDSETS

Your wellness starts now!

Gender    ○ Male  ● Female

Age       [47]

Weight    [140] Lb

Goal Weight  [130] Lb

Height    [5 ▾] Ft  [4 ▾] In ( SEND > )

Setting Your Goal Weight

Rome wasn't built in a day, and neither were you! It took a while to gain it, so cut yourself some slack when it's time to lose it. Instead of one BIG goal, set several smaller goals (like 10-15 pounds at a time).

Every pound lost means using 3500 more calories than you take in. Exercise helps burn the calories and gets you to your goal faster.

HOME · WHY Sensei · ARTICLES · RECIPES · HEALTH TOOLS · FAQ · About Sensei · JOIN    MY Sensei.com (login)

Sensei  CHANGING MINDSETS WITH HANDSETS

Join Sensei

Step 2
Account Details

You know the drill. Fill in the blanks.

Pick a username and password.

We'll send you a confirmation by email.

Your credit card will be charged monthly for the term of your Sensei contract. You can cancel at any time by contacting customer support.

Choose a username (8 chars limit) Check username availability
[_____] — 202

Confirm your password
[_____]

Choose a password
[_____]

Email address
[_____]

Security Question
[..........................]

Security Answer
[_____] — 204

First Name
[_____]

Last Name
[_____]

Street Address
[_____]

City
[_____]

State
[Choose: ▾]

Zip Code
[_____]

Country
[United States ▾]

FROM FIG-2B1

Birthdate
Month [v] Date [v] Year [v]

Phone (xxx-xxxxxx)

Mobile Manufacturer [v]

Mobile Carrier [v]

Mobile Number (xxx-xxxxxx) — 206

Mobile Model [v]

☐ I have read and agree to the Terms of Use.
☐ I have read and agree to the Medical Disclaimer.

(Submit >)

FIG-2B2

*mySensei* CHANGING MINDSETS WITH HANDSETS

Hello
My Diet Plan                    SIGN OUT | ACCOUNT SETTINGS

Your life needs balance. Your diet needs balance.

Balance, portion control, and increased activity are the core of healthy living. Each plan is a balanced approach to nutrition providing some variations in taste and interests.

All the Sensei's meal plans are healthy, will help you lose weight, and keep it off for a lifetime.

Choose the plan that fits your life Remember:
Extremes like starvation or deprivation aren't successful or healthy.
Starvation leads to hibernation, slows your metabolism, and slows your weight loss. Avoiding carbs or fats will only make you crave them more.

SENSEI SENSEIBLE/BALANCE PLAN — 208

→ CHOOSE

Reduces calories by cutting down fat and sugar
Includes a variety of foods (such as fruits, vegetables, and grain)
Convenience foods easily fit into this plan
Based on 2005 Dietary Guidelines

MORE...

SENSEI HEALTHY CARB PLAN

→ CHOOSE

A healthier version of popular low carb diets
Includes more lean meat, fish, dairy, nuts
Decreases less healthy carbs and keeps good ones
Limits sweets and baked goods
Convenience foods fit into this diet plan

MORE...

SENSEI MEDITERRANEAN PLAN

→ CHOOSE

Includes fish, grains, fruits, vegetables, beans and nuts
Major fat is olive oil (monounsaturated) and other unsaturated fats
Some convenience foods may not fit
Some meals can require a little more preparation time for some meals (but we do have Quick & Easy choices too)

MORE...

FIG-2C mySensei CHANGING MINDSETS WITH HANDSETS

Hello
SIGN OUT | ACCOUNT SETTINGS

Food Filter

→ SAVE AND CONTINUE — 212

Don't Send Me These!

We promise not to make you eat foods you don't like. Check off the foods that you avoid and we'll keep them out of your menus. Click the box to select a whole food category or click the icon to expand the list and pick certain foods in each group.

☑ – Category fully selected   ☒ – Category partially selected
☐ – Category empty ☑ Meat, Poultry and Fish          ☒ Beans, Nuts and Seeds ☐ Grains & Soy Products           ☐ Fruit ☐ Vegetables                       ☐ Dairy ☒ Condiments and Dressings Other Foods or Dishes Don't see something you're looking for? Type the first letters in a box below and a list of choices will come up. Click the one you want and we'll take that off your menus.

*my*Sensei CHANGING MINDSETS WITH HANDSETS

Hello
SIGN OUT | ACCOUNT SETTINGS

Meal Times

↑ SAVE AND CONTINUE — 214

Menu's ready!
You'll have 3 meals and 1 snack on the Sensei program. Schedule your meals every 4-5 hours so you don't go too long without eating.

You will hear from us about 1/2 hour before your meals and snacks.

|  | Weekdays | | | Weekends | | |
|---|---|---|---|---|---|---|
| Breakfast | 7 ˅ | :30 ˅ | AM ˅ | 8 ˅ | :00 ˅ | AM ˅ |
| Lunch | 12 ˅ | :15 ˅ | PM ˅ | 12 ˅ | :00 ˅ | PM ˅ |
| Dinner | 6 ˅ | :30 ˅ | PM ˅ | 6 ˅ | :30 ˅ | PM ˅ |
| Snack | 10 ˅ | :00 ˅ | PM ˅ | 10 ˅ | :00 ˅ | PM ˅ |

↑ SAVE AND CONTINUE

FIG-2E mySensei CHANGING MINDSETS WITH HANDSETS

Hello
SIGN OUT | ACCOUNT SETTINGS

My Meal Preparation

Your Meals Your Way
Choose the preparation that best suits you and your lifestyle. You can change your preferences at any time.

Quick & Easy: <10 min prep; soups, sandwiches, salads

Cook at Home: >10 min to fix; grilling, baking, stir frying. Make ahead to save time.

Frozen/Ready to go: frozen meals, prepackaged refrigerated meals, open & eat canned goods, & other portable foods. Great for portion control!

Fast Food: salads, small plain burgers, sandwiches, fruit. *Options are limited and may not follow Sensei diet plan you choose.*

Go Out/Order In: what to order when eating out. Restaurant portions are big-be prepared to take home leftovers or share.

We will automatically send you snacks that are simple to make, so no need to select a preparation for these.

Select Preparation Type (Drag and Drop) — 216

| Quick & Easy | Cook at Home | Frozen/Ready to go | Fast Food | Go Out/Order In |

— 218

| | Breakfast | Lunch | Dinner |
|---|---|---|---|
| Weekdays (Mon-Fri) | | | |
| Weekends (Sat-Sun) | | | |

⇧ SAVE AND CONTINUE

⇧ SAVE AND CONTINUE

FIG-2F

My Behaviors

Changing old habits is HARD! If it was easy, we'd all be fabulously thin! Weight loss isn't just about food, and eating isn't always about hunger. Sensei goes beyond the typical diet plan to focus on eating habits you'd like to change. Habits are behaviors we learn through repetition. To change them requires focus, determination, and repetition of positive behaviors. Think of some challenges you might have, and let's work on them together to build positive habits.

⇥ SAVE AND CONTINUE

My Biggest challenges in healthy eating is that I have always...(Choose 3) — 220

- ☐ Eating when I am stressed
- ☑ Eating in front of the television or when I use the computer
- ☐ Snacking late at night
- ☐ Being an emotional eater (happy and/or sad)
- ☐ Eating when I am bored or don't have things to do
- ☑ Eating too many sweets/snacks at work
- ☑ Being tempted to eat food when it is just there, even if I am not hungry
- ☐

Of your challenges, pick one to work on first — 222

- ⦿ Being tempted to eat food when it is just there, even if I am not hungry
- ○ Eating too many sweets/snacks at work
- ○ Eating in front of the television or when I use the computer

FROM FIG-2G1

Here are a list of strategies to help you. Pick 1 that fits your lifestyle best

○ Reach for some sugar-free gum to keep your mouth busy without calories
○ Keep snacks in hard to reach places like the top shelf of the cupboard, behind the paper towels
○ Boredom=snacking. Get busy
○ Out of sight, out of mind. Keep hard to resist foods out of the house! If you have to snack, at least let it be healthy.
○ Exercise! Activity is the healthiest way to occupy your time
○ Call a friend and spend time catching up
○ Don't leave food on display–that can trigger an urge.
○ Keep a sugar-free drink handy, staying hydrated can help manage an urge to munch
○ Distract your attention by doing a chore–if at home, clean 1 room in the house
● Head outside for a walk to clear your head and refocus on something other than food

Jane Smith, we're ready to help you reach your weight goal of 130lbs.

Nutrition

Your diet plan:

SENSEI SENSEIBLE/
BALANCE PLAN

Your food filter:

> Meat, Poultry and Fish
> Nuts & Seeds (all)
> Olives

Your meal preparations:

| | Breakfast | Lunch | Dinner |
|---|---|---|---|
| Weekdays | | | |
| Weekends | | | |

Fitness — 242

Exercise is one of the most powerful things you can do for your health. It's a no-brainer; regular activity along with a healthy diet is the best way to lose weight and maintain it for the long haul.

It's great that you're already doing some exercise. Based on what you told us, we've put together the following exercise program to help you improve your fitness level:

Cardiovascular activities:

| Bicycling | Walking |
|---|---|

Days of activity:

Over time, we will help you increase your duration and frequency so you are doing more.

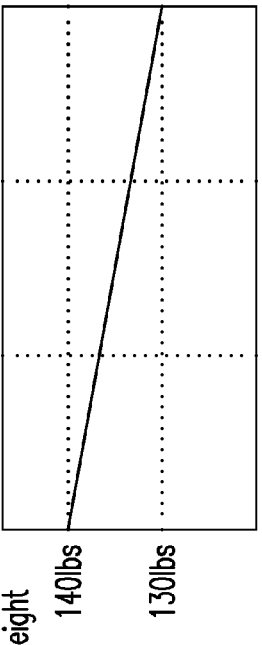

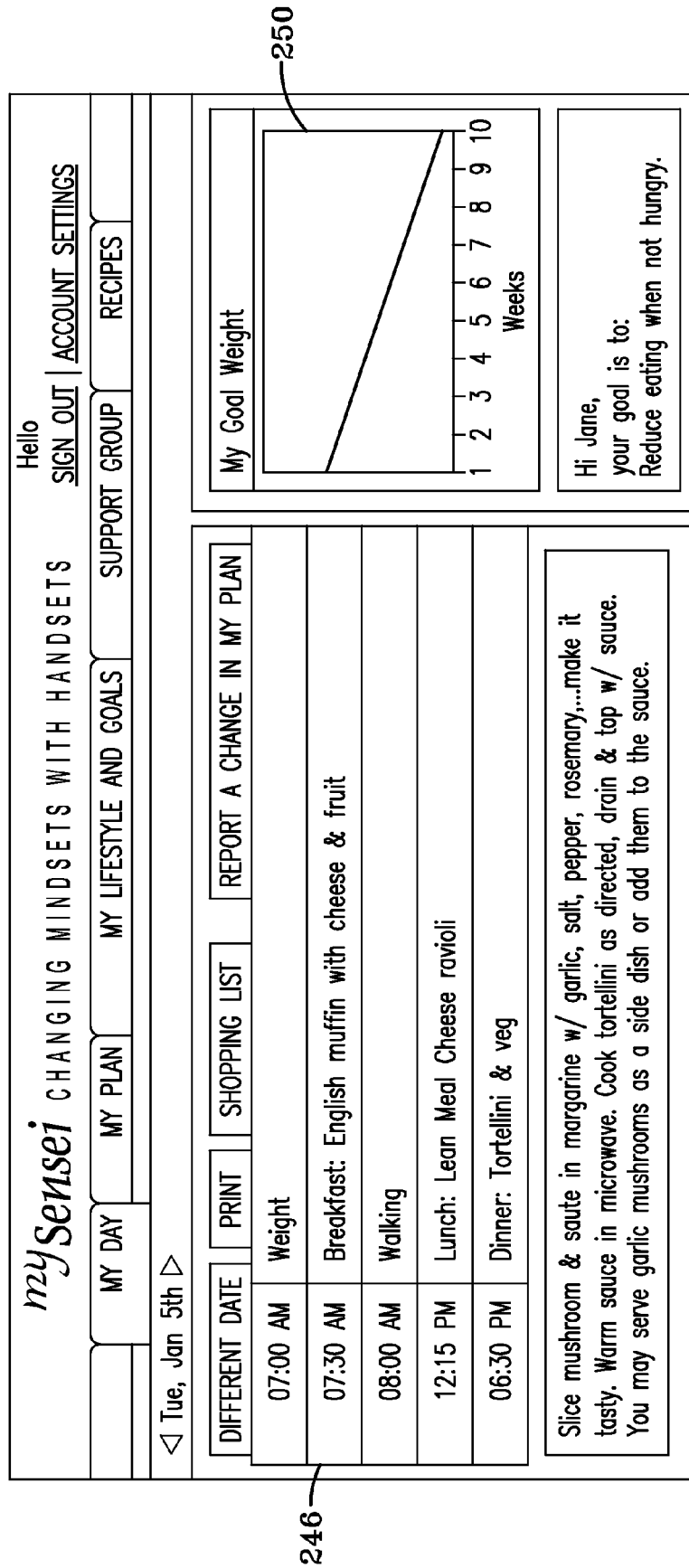
FIG-2K1

FROM FIG-2K1

Click on any ingredient for info and substitutions

1 Cup Cheese tortellini (332kcal)

0.5 Cup Spaghetti sauce cnd (60kcal)

1 Each Portabella mushroom, fresh (27kcal)

1 Teaspoon Margarine red. cal (50cal/Tbsp) (17kcal)

CHANGE THIS MEAL

Total meal calories: 436 calories

| 10:00 PM | Snack: Papaya |

Total day calories: 1200 calories

248

Today's Tip

Put a picture on the fridge of something that motivates you... your children, a thinner you, friends...you decide.

From Sensei Library

Dieting Does Not Equal Deprivation

Do you feel deprived every time you start a diet? That might be one of the reasons that diets don't last!

Check our blog: Sensei Thoughts.

Here is where the Sensei team will share thoughts on what's happening in the world of health and wellness.

New In My Groups

FIG-2K2

*my*Sensei CHANGING MINDSETS WITH HANDSETS

Hello
SIGN OUT | ACCOUNT SETTINGS

| MY DAY | MY PLAN | MY LIFESTYLE AND GOALS | SUPPORT GROUP | RECIPES |

MY DIET | MY FITNESS | MY FOOD PREFERENCES

My Diet Plan

| My Plan | CHANGE PLAN | MON | TUE | WED | THU | FRI | SAT | SUN | PRINT MY DIET PLAN |
|---|---|---|---|---|---|---|---|---|---|
| SENSEI SENSEIBLE/ BALANCE PLAN | | 07:30 AM | | Breakfast: English muffin with cheese and fruit — 252 | | | | | |
| | | 12:15 PM | | Lunch: Lean meal Cheese ravioli | | | | | |
| | | 06:30 PM | | Dinner: Tortellini & veg | | | | | |
| | | 10:00 PM | | Snack: Papaya | | | | | |

Your Guidelines

Reduces calories by cutting down fat and sugar.
Includes a variety of foods (such as fruits, vegetables, grain).
Convenience foods easily fit into this plan.
Based on 2005 Dietary Guidelines.

FIG-2L

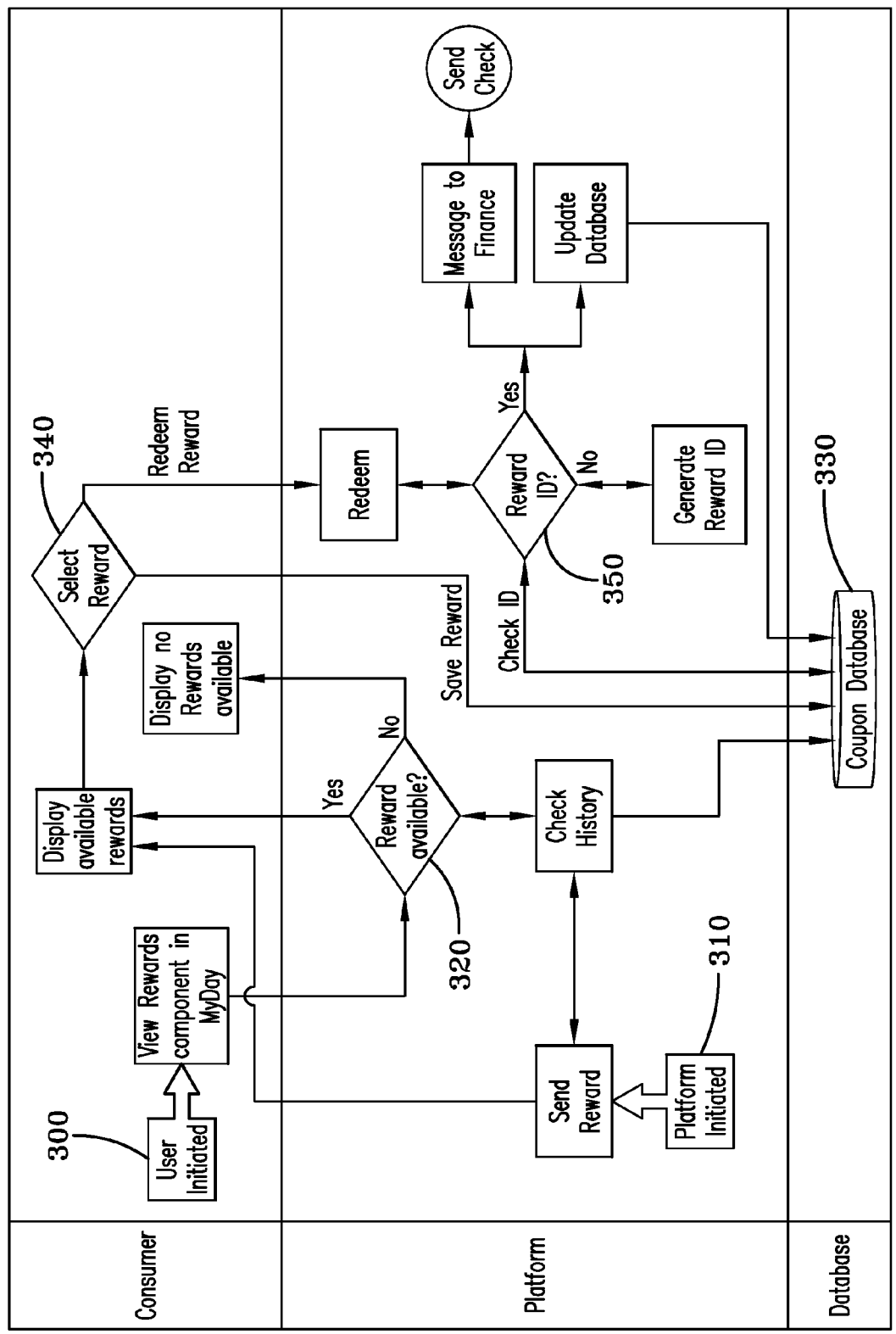

SYSTEM AND METHOD FOR REWARDING USERS FOR CHANGES IN HEALTH BEHAVIORS

CROSS-REFERENCE TO RELATED APPLICATIONS

None.

TECHNICAL FIELD

The present invention relates generally to systems and methods for assisting with the maintenance of healthy lifestyle habits. More particularly, the present invention is a system and method for rewarding users for changes in their health care behaviors and habits.

BACKGROUND AND SUMMARY OF THE INVENTION

Many people are affected by a variety of health problems including obesity, diabetes, high blood pressure, and elevated cholesterol levels which can be linked to poor habits in diet, exercise, and the like. Although people are generally aware that controlling diet, exercise, and similar lifestyle habits is the easiest way to become or stay healthy, getting them to adopt and maintain these habits is a difficult task. Many people do not have access to information or to systems or methods that can effectively assist them in these challenging endeavors.

Dieting has become an extremely popular activity resulting from people's awareness of the health risks of becoming overweight or obese, a desire to improve one's appearance, and an aspiration to achieve the sense of accomplishment that comes from setting a difficult goal and accomplishing it. However, there is no singular method of dieting that works for every person. Body types, weight loss goals, and preferences vary greatly depending on the individual. Every dieter has individual likes and dislikes as to types of food, times and places to eat, type and length of exercise, eating habits, etc. Due to these differences, many dieters become frustrated with rigid, impersonal diets, and often quit the diet after a short time.

Furthermore, dieters differ on how well they can motivate themselves to continue to adhere to certain dietary guidelines. For example, a dieter who is supposed to only eat a cup of pasta and a vegetable for lunch, but instead decides to eat an ice cream cone as well may be unable to justify such a decision within the diet and decide to give up the diet for the rest of the day. Because such "splurges" are detrimental to the dieter's physical and mental progress, the dieter may find the diet unsustainable.

Known regimes often require individuals to determine what to eat and when to eat as well as calculate the calories they have consumed (e.g., by determining the calorie count of all foods or adding points that are tied to the calorie counts of certain foods) and they must keep an exercise record and determine the caloric impact of their exercise on their overall regime. Current diet and exercise regimes typically restrict severely the types of food individuals can consume or the types of activities in which they are guided to participate. This lack of variety causes individuals to become frustrated with their regimes and to give up before they have experienced their desired results.

There are a few known methods and systems for assisting individuals with the maintenance of healthy lifestyle habits, but these methods and systems are expensive and often inaccessible to most people. For example, a highly effective method for assisting individuals in developing and maintaining healthy lifestyle habits is found through the use of coaching. Research has shown that individuals are more successful in the difficult endeavor of changing their habits and maintaining new, healthier ones when they are coached throughout the process. Coaching keeps individuals motivated, provides positive reinforcement, and introduces a narrowly-tailored plan, usually with specific intermediate goals, for each individual participant. However, obtaining a reliable human coach is difficult and often prohibitively expensive such that relatively few dieters are actually able to use one. In addition to purchasing the services of a human coach, it has been shown that the services of a personal chef, who is trained in preparing healthy meals, and/or those of a nutritionist, who is able to develop a personalized diet plan, are successful methods for an individual to be assisted in maintaining healthy lifestyle habits, but these methods are also expensive and thus inaccessible to many.

The present invention relates generally to systems that promote healthy lifestyles and, in some embodiments, to weight loss systems. The present invention is an improvement upon existing health behavior systems in that it provides an enhanced support system to help users follow a personalized plan. The present invention may be used to motivate dieters as well as keep them on a healthy diet while at the same time allowing flexibility in different dieting aspects including, but not limited to, types of food, types of food preparation, amount of food, and amount of exercise.

The present invention addresses the diet and exercise problems identified above by providing personalized plans to meet the needs and requirements of individuals. It uses tailored messages to "coach" individuals in following their personalized plans. An expert system uses information about an individual's diet and exercise preferences to provide tailored messages related to the plan. The individual receives personalized instruction in the dieting field, without having to pay the prohibitively expensive fees that are typically associated with personalized instruction. Exemplary embodiments of the present invention allow the individual to use portable devices and technology, such as cell phones, PDA's, Blackberrys™, iPhones™, and others, so that the individual has constant access to personalized instruction regarding his or her personalized diet and exercise plan.

It has been found, through the study of behavior informatics, that the use of technology can help people make significant changes in their health. Gradual change, over a longer period of time, is more effective for long-term health solutions, rather than behavior changes that are expected to take place rapidly, over a short period of time. Further, many dieters are more comfortable using familiar technology to assist them with their dieting, as opposed to unfamiliar and possibly uncomfortable office and training room sessions with an actual dietitian and trainer. The present invention incorporates these concepts into a diet and exercise instructional platform based on individuals' preferences to increase the likelihood that individuals will adopt and follow a plan that helps them reach their personal goals.

In an attempt to make the services of coaches, nutritionists, personal chefs, and the like accessible to those who could not afford them otherwise, many books have been written and/or home videos produced that focus on disseminating the type of expert information these individuals typically offer their clients. Unfortunately, those who invest in these books and/or videos are noticeably less likely to maintain the healthy lifestyle habits they aim to encourage than those who invest in the actual expert services. The mass marketed materials are aimed at a wide audience and cannot meet the needs of each individual purchaser. The difference that actual health and fitness experts can provide is the ability to provide their clients with appropriate strategies and plans tailored to the individual thereby reducing or eliminating the various barriers to success.

In light of these foregoing problems with known systems and methods, there is a need for a generally affordable and accessible system and method that assists in the maintenance of healthy lifestyle habits by providing individual users with a diet, exercise, or other health regime specifically tailored around their personal preferences so that they are not restricted to the point that they become frustrated thus discontinuing their practice of the regime's healthy habits. Additionally, there is a need for a system and method that assists individual users in determining what activities they should be completing and when. For example, in the area of dieting, there is a need for a system and method for assisting users with determining what foods to eat and when to eat them. The system and method should account for an individual user's preferences. Furthermore, the system and method should provide individual users with personalized guidance, strategies, and support similar to that which can be provided by health, fitness, and other behavioral experts in order to maximize the probability that individuals will successfully maintain healthy lifestyle habits. Finally, the system and method should reward users when they reach intermediate and specific goals so they are motivated to continue with the plan. Keeping individuals motivated is important in helping them achieve lifestyle changes.

The present invention is a system and method for assisting with the maintenance of healthy lifestyle habits by generating tailored messages within an expert system and then pushing those messages to the corresponding individual users. The system and method of the present invention utilizes modern technologies, such as the cellular phone or other portable device, to facilitate the pushing of the tailored messages from the system's computer-based expert system to the individual users. Users provide personal information and commit to reaching specific goals or responding to specific challenges. Messages to users are directed to changing their health behaviors. Users are encouraged to reach an ultimate goal by reaching a series of intermediate goals while establishing healthy habits. Users are rewarded for intermediate goals and for overcoming challenges they face to help keep them focused on a lifestyle change.

In an example embodiment of the present invention directed to diet and exercise, plans are tailored to individual users based on their preferences, challenges, and goals. The system and method provides consistent and appropriate strategy messages for goals and challenges designed to encourage and motivate users toward successfully developing and maintaining healthy lifestyle habits. The personalized instruction of the present invention is based on an individual's diet plan preferences, food preferences, meal preparation preferences, and exercise preferences. Once the dieter's plan has been established, typically by providing preference and other information through an online website, the dieter is never required to access the site again as the personalized instruction is given through the dieter's portable technology. The prior art is known to center around "pull" technology, where the user must reach out to the system for the information, and if there is inaction by the user, the instruction will stop. Embodiments of the present invention utilize "push" technology, where the instruction is sent to the user, and inaction by the user will prompt the system to reach out to the user, for corrective actions and encouragement. Exemplary embodiments allow the individual user to utilize portable technology, such as cell phones, handheld computing devices, and personal digital assistants (PDA), so that the user has constant access to their personalized instruction and support.

In the present invention, rewards are incorporated into the personalized messages for each user. The rewards provide an incentive to the user to follow the personalized plan and to set and reach new goals or to overcome challenges. Rewards may be given for a number of reasons such as achieving an ultimate goal, losing a certain percentage of a prior bodyweight, losing a certain number of pounds, substituting a healthier meal for a suggested meal, eating healthy foods for a consecutive number of days, exercising consistently, or achieving a certain waist size. A reward may be a coupon or a check that is sent through the postal mail or a coupon that can be printed from the user's home printer. The rewards may also be permission for the user to enjoy a favorite food that is not part of the user's meal plan due to its unhealthy characteristics.

In addition to the novel features and advantages mentioned above, other features and advantages will be readily apparent from the following descriptions of the drawings and exemplary embodiments.

BRIEF DESCRIPTION OF THE DRAWINGS

FIG. 1 illustrates the physical structure of a system according to an example embodiment of the present invention.

FIGS. 2A-2L are screen shots for completing a user profile and specifying preferences according to an example embodiment of the present invention.

FIG. 3 is a logic flow of a reward system according to an example embodiment of the present invention.

DETAILED DESCRIPTION OF EXEMPLARY EMBODIMENT(S)

Figure 2H:

FIG. 1 is an illustration of a physical structure for an example embodiment of the present invention. Connections between components permit data to flow in both directions. A laptop or desktop personal computer 100 is connected to a server 120 through the Internet 110. The server 120 is connected to one or more databases 122, 124 comprising user data, nutrition provider data (nutritional data related to meals offered by a plurality of meal providers), diet, and exercise data, message data, progress data, compliance data, restaurant, shopping, and entertainment establishment data, reward data, and other data as may be required to provide the features and functionality of the present invention. The server 120 is connected to communication networks 130 through the Internet 110. The various communication networks 130 facilitate communications with user portable technology 140 which includes cellular or mobile phones, personal digital assistants, or any other portable device capable of sending and receiving communications through the communication networks 130 and displaying them for a user. An expert system at the server uses the individual's account information, including information about the individual's mobile phone, to tailor and send to the individual messages to reinforce and motivate healthy habits.

In a preferred embodiment, the expert system is constructed using the J2EE programming language in conjunction with a SQL based database (like Microsoft SQL Server or Oracle DB). AJAX, Active X and Java components may also be used to handle various aspects of the system. The mobile component of the overall system is constructed using the J2ME programming language sending wireless requests to the expert system over common carrier communication protocols. Communication between the mobile component and the expert system is constructed using XML language structures.

The present invention is designed to encourage and motivate users towards successfully maintaining healthy lifestyle habits by pushing tailored messages, including reward messages, from a computer based expert system to individual users via cellular technologies. The system incorporates the personal preferences of individual users in regard to health behaviors such as diet, exercise, and other similar habits in conjunction with personal information such as age, weight, gender, and desired results as well as behavioral challenges in order to generate personalized and tailored messages to assist individual users with the adoption and maintenance of healthy lifestyle habits.

Tailored messages according to the present invention generally belong to one of the following categories:

TABLE 1

| Message Type | Message Content |
| --- | --- |
| Suggestion/Advice | Message comprising content relating to an activity to be performed at a specified time (e.g., breakfast meal suggestion, lunch meal suggestion, dinner meal suggestion, food substitution message, physical activity message) |
| Education | Messaging comprising factual content (e.g., calories in suggested food, transfat in suggested meal, calories burned during specified activity) |
| Feedback | Message comprising content regarding an individual's progress toward a specified health goal |
| Motivation/Praise | Message comprising content encouraging an individual to continue activities related to health goals or overcoming challenges |

Other types of health and goal related messages that are generated and sent to individuals may include content from more than one category or may not correspond directly to the specified categories. The expert system of the present invention can generate a variety of types of messages that are directed to changing a health behavior and to assisting individuals in reaching their specified goals and in developing healthy lifestyle habits. Reward messages may be used to remind users of successes they are experiencing in changing their lifestyles and to provide incentives to follow their personalized plan. Messages may be timed according to each user's preferences and challenges to help them establish and maintain a healthy lifestyle.

Referring to FIGS. 2A-2L, screen shots for completing a user profile, specifying diet and exercise preferences, and identifying health behavioral challenges in an enrollment process according to an example embodiment of the present invention for diet and exercise are shown. The user provides contact and background information, specifies a weight goal, specifies preferences related to diet and exercise, and identifies personal behavioral challenges. The user's profile data and specified goal and diet and exercise preferences are considered by the expert system of the present invention to generate personalized and tailored messages intended to reinforce and motivate behaviors that are important in helping the user reach the specified goal. The user accesses a website to navigate through the screens and provide data and information that allows the system to build a profile for the user comprising, for example, diet and exercise preferences as well as behavioral challenges.

Referring to FIG. 2A, a screen for specifying physical characteristics and a weight goal is shown. The user specifies a sex, age, weight, and height and a goal weight 200. This information is saved in the user's profile and used to determine the user's progress toward the goal. The expert system generates tailored messages that help the user to progress toward the specified goal and arranges to send the tailored messages based on the user's personal preferences and challenges.

Referring to FIG. 2B, an account screen for an example embodiment of the present invention is shown. First, the user specifies a username, password, and email address to create an account 202. Next, the user provides contact information 204. The user also provides information about his or her mobile phone or other portable device so that messages from the expert system of the present invention can be pushed to the portable device 206.

Referring to FIG. 2C, a diet plan screen for an example embodiment of the present invention is shown. The user specifies the type of diet plan he or she would like to follow. In an example embodiment of the present invention, the user may select from one of three diet plans 208. A first plan is a balanced plan which emphasizes a diet of reduced calories as well as reduced fat and sugar. A second plan is a healthy carbohydrate plan that emphasizes a diet of lean meats, fish, dairy, and nuts. A third plan is a Mediterranean plan that emphasizes a diet of fish, grains, fruits, vegetables, beans, and nuts.

Referring to FIG. 2D, a food preference screen for an example embodiment of the present invention is shown. The user selects a food category and identifies the foods in each category that he or she does not like or wants to avoid 210. In an example embodiment of the present invention, the categories include: 1) meats, poultry, and fish; 2) beans, nuts, and seeds; 3) grains and soy products; 4) fruit; 5) vegetables; 6) dairy; and 7) condiments and dressings. Within each category, the user can select from a list the foods he or she does not want to eat. Alternatively, an entire category of food can be selected. Finally, if the user does not find a particular food on any list within a category, the specific food can be entered in a text box 212. As the user types, choices matching the entered text are presented. Foods identified in the text boxes as well as foods selected from the category lists are not included in any menu or meal suggestions that are provided to the user.

Referring to FIG. 2E, a meal times screen according to an example embodiment of the present invention is shown. The user specifies a time of day for eating breakfast, lunch, and dinner as well as a snack 214. The user specifies two sets of meal times, one for weekdays and one for weekends. Referring to FIG. 2F, a meal preparation preference screen according to an example embodiment of the present invention is shown. On this screen, the user specifies preferences related to meal preparation options 216. Using a drag and drop feature, the user specifies meal preparation preferences for breakfast, lunch, and dinner on weekdays and weekends 218. In an example embodiment of the present invention, the meal preparation options are: 1) quick and easy (fewer than 10 minutes to prepare); 2) cook at home (more than 10 minutes to prepare); 3) frozen or ready to eat; 4) fast food; or 5) order from restaurant. The meal preparation preferences provide additional data for the expert system to consider when generating messages to the user related to meal options.

Referring to FIG. 2G, a behavior challenges screen according to an example embodiment of the present invention is shown. The screen presents common challenges or difficulties in attaining and maintaining a healthy lifestyle 220 and allows the user to select the ones that are applicable. The user is also asked to identify the challenge he or she would like to overcome first (a priority challenge) 222. Finally, the screen presents a list of strategies for overcoming common challenges 224. The user is asked to select a strategy that is appropriate for the user's lifestyle. The user's selections related to applicable challenges, a priority challenge, and a challenge strategy are considered by the expert system in generating tailored messages. As user's address the challenges they face, they make progress toward their intermediate and ultimate goals and toward maintaining a healthy lifestyle.

The expert system determines times for sending messages based on the types of challenges that user's identify. For example, if a user identifies between meal snacking or nighttime snacking as a challenge, the expert system sends messages at times that a user might ordinarily snack to help the user focus on another type of activity. Reducing or eliminating snacks can be an important step in helping a user to reach a weight goal.

Figure 2I:
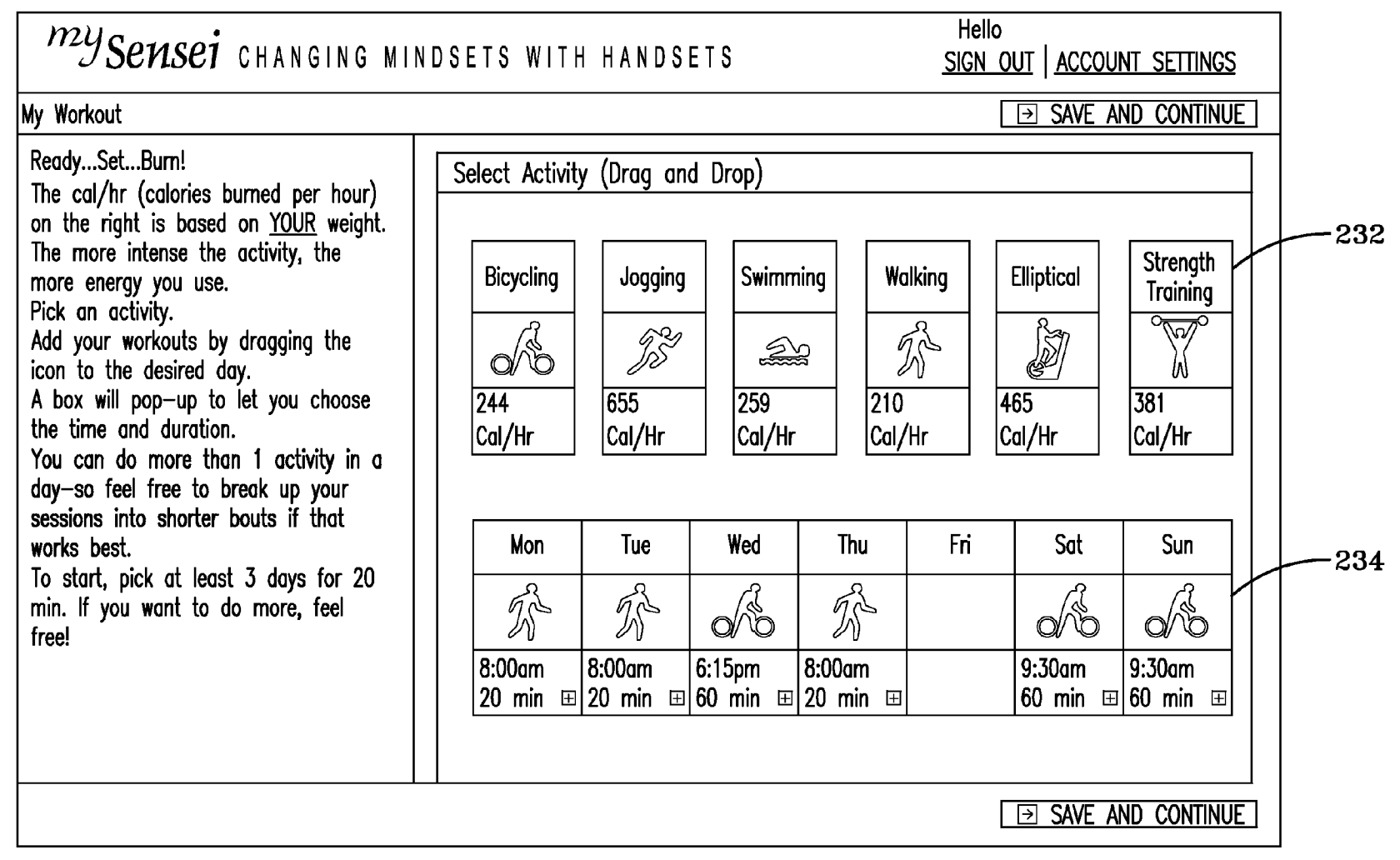

Referring to FIG. 2H, an activity screen according to an example embodiment of the present invention is shown. The user provides information about his or her current activity level 226 and exercise frequency 228. In addition, the user indicates whether he or she smokes 230. The user's selections related to current activity level, exercise frequency, and smoking are considered by the expert system in generating tailored messages. Referring to FIG. 2I, a workout screen according to an example embodiment of the present invention is shown. Using a drag and drop feature, the user identifies preferred physical activities 232 and specifies times for performing the physical activities on a weekly basis 234. The preferences related to physical activities and times are considered by the expert system in generating tailored messages.

Referring to FIG. 2J, a profile overview screen according to an example embodiment of the present invention is shown. The screen presents information regarding the data and preferences specified by the user while completing the profile data entry screens. A nutrition section comprises the user's selections related to a diet plan and specific food preferences 236 as well as meal preparation preferences 238. A weight section comprises the user's personal data related to current weight and body mass index as well as goal weight (ultimate goal) and proposed rate of weight loss per week 240. The proposed rate of weight loss may be used to establish intermediate goals or milestones for the user to reach. A fitness section comprises the user's selections related to physical activity preferences 242. A behavior section comprises information about the user's priority challenge and preferred strategy from overcoming the challenges he or she specified previously 244.

Referring to FIG. 2K, a daily plan screen according to an example embodiment of the present invention is shown. The daily plan screen presents a complete schedule of activities and meal suggestions based on the personal data and preferences specified by the user previously 246. In the example schedule, the user takes a weight reading at 7:00 AM, eats the suggested breakfast at 7:30 AM, completes the suggested activity at 8:00 AM, and eats the suggested lunch and dinner at the specified times. The daily plan screen also presents food substitution suggestions in the event the user does not want to follow the initial meal suggestion. The user can select any ingredient in the specified meal suggestion and select a substitution. The ability to substitute ingredients in a specified meal allows the user to change the meal only slightly or to change the entire meal to meet his or her preferences at mealtime. Referring to FIG. 2L, a diet plan screen according to an example embodiment of the present invention is shown. At this screen, the user can review the weekly meal suggestions 252 and complete any substitutions prior to receiving the meal suggestions at the mobile phone or other portable device.

FIG. 3 is a logic flow of a reward system according to an example embodiment of the present invention. The reward system may be user initiated 300, when a user requires access to available rewards, or platform initiated 310, when the system sends available rewards to the user. When the system is user initiated 300, the reward available logic box 320 checks a coupon database 330 for rewards availability. The user may access the reward system through portable technology 140 or a personal computer 100, shown in FIG. 1. The coupon database may be one of the databases connected to the server/mainframe 120, also shown in FIG. 1.

If the coupon database 330 shows available rewards, the reward available logic box 320 returns a yes, and the system displays the available rewards. If the coupon database 330 shows no available rewards, the reward available logic box 320 returns a no, and the system displays that no rewards are available. Once the system reaches the select reward logic box 340, the user has the option of either saving or redeeming the available rewards. If the rewards are saved, they will return to the coupon database 330. If the rewards are redeemed, the system continues to the reward ID logic box 350.

Rewards that are redeemed are issued an identification number (ID) for tracking purposes, such as ensuring that duplicate rewards are not issued to the same user, preventing fraudulently obtained rewards, and ensuring that rewards are actually sent and received by the user. The reward ID logic box 350 first accesses the coupon database 330 to determine if an ID exists for the reward about to be redeemed. If no ID exists, then one is generated. Once an ID exists, a message is sent to a finance department and a reward is issued to the user. Additionally, a feedback loop returns to the coupon database 330 to remove the issued reward from the database of available rewards.

Using a portable technology platform facilitates the incorporation of other technologies such as location-based services (e.g., GPS) to expand the scope and reach of available rewards under the present invention. Portable technology contains location based technology such as GPS, and allows embodiments of the present invention to use this technology for messaging purposes. For example, knowing the location of the user allows the system to suggest restaurants and markets in the area, and further suggest specific meals or offer rewards at nearby establishments. This location based technology may also suggest nearby parks for recreation, and can detect the number of times a user has visited a certain restaurant, store, park, fitness center, or other establishment. Rewards may include coupons or certificates for restaurants or other entertainment or shopping establishments close to the user at the time a reward is issued. Coupons or certificates that are issued may be for discounts on meals at the user's favorite restaurants, clothing at various clothing stores, exercise equipment, or meals and foods at markets and grocery stores. Rewards may also be cash rewards such as checks or cash cards. The reward message is personalized not only with respect to the user's personalized diet and exercise plan, but also with respect to the user's current location. As a result, the user may be encouraged to continue with the plan and to reach another goal with the hope that another reward personalized according to content as well as location will be issued.

The system automatically tracks the user's progress and rewards that are offered as the user makes progress toward a goal. The expert system may develop one or more milestones for the user to reach while making progress toward an ultimate weight or exercise goal. The expert system may send progress messages to the user and periodically request progress data that is used to determine the type and timing of a reward. The progress data may be the user's current weight or another measurement, or it may be information about a completed activity such as eating a suggested meal or performing a suggested physical activity. Once a milestone is reached, a reward message is sent to the user.

Rewards may also be used to help users overcome behavioral challenges they face on a daily basis. For example, a user that typically eats a nightly snack may be rewarded when he or she foregoes a nightly snack. Another user that has difficulty completing a physical activity for a specified period of time may be rewarded when the physical activity is completed for the specified time.

The user may view the available rewards at any time from his or her portable technology or through the system website. Rewards may be combined and exchanged for other rewards. From the constant interaction with the user, the expert system of the present invention knows which foods, meal preparation options, stores, etc. the user prefers, and will issue rewards based on the user's preferences. For example, when issuing to the user a shopping list for purchasing ingredients necessary to prepare a suggested meal, coupons for the associated ingredients may be sent simultaneously. This approach not only rewards the user for past behavior but also provides an incentive to purchase the discounted ingredients in order to prepare the suggested meals and continue progress toward a goal. Furthermore, with the use of location-based services, the expert system can learn the present location of the user and the paths that the user typically takes (e.g., from home to the office, from home to the gym, etc.) and will issue rewards to locations nearest the user or located directly on one of the user's typical traveling routes. Location-based services may also be used to verify the user's response to meal or other suggestions. For example, if the user accepts a suggestion of a restaurant or entertainment or shopping establishment but never enters a five mile radius of the restaurant, the expert system may prompt the user for a correction.

Reward messages are generated by the expert system as follows. Reward messages contain an appropriate reward based on how the message was generated. Rules for message generation include:

Motivation is an important factor in helping a user achieve a weight loss or other health behavior goal. Rewarding a user for successful progression through intermediate steps of a personalized plan provides an incentive to continue the plan until the user reaches an ultimate goal. The "push" technology of the present invention is extremely beneficial to users in that when user interaction slows or stops, (e.g., no responses to any meal suggestions or no manual entries over a period of time), the expert system continues to contact the user, giving messages of encouragement to continue the plan. Rewards according to the present invention provide another reason for contacting a user and reminding the user of successes as they occur. This approach is advantageous over prior art approaches where inaction by the user causes all interaction between the user and system to stop, possibly causing the user to abandon the plan.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to affect the described invention. Many of those variations and modifications will provide the same result and fall within the spirit of the claimed invention. It is the intention, therefore, to limit the invention only as indicated by the scope of the claims.

What is claimed is:

1. A computerized method for automatically generating a reward message for a user who accomplishes an intermediate milestone based on an ultimate goal, the computerized method comprising:
(a) receiving at a computer from said user:
  (1) an ultimate goal;
  (2) activity preferences related to said goal; and
  (3) contact data for a mobile device of said user;
(b) storing at said computer said ultimate goal and said activity preferences for said user;

TABLE 1

| | |
|---|---|
| Meal Time (Coupons based on recommended or solicited meal, meal specific, filtered by LBS and promotions available in database) | Coupon generated based on change of meal or meal preparation option Tied into location based services module to map users location to nearby restaurants and offer a meal coupon for associated restaurants |
| Behavior goals | Reward generated based on success criteria associated with the behavior goals Success criteria (defined on a number scale 1, 2 or 3) varies per response to goal attainment message |
| Objectives | Reward generated when a major milestone is attained Reward based on behavioral information from system/carrier. Exchange program for reward system (reward substitution) |
| Shopping list | Rewards (coupons) generated on a weekly basis Rewards distributed with the shopping list email (food item specific sorted by group parallel to shopping list) Rewards available from the mobile phone for redemption while/after weekly shopping complete |

(c) executing at said computer an expert system that automatically
   (1) generates at said computer at least one personalized intermediate milestone for said user, said personalized intermediate milestone:
       different than said ultimate goal; and
       consistent with said user's personal data;
   (2) generates at said computer at least one progress message comprising a request for a progress measurement from said user;
   (3) using said contact data from said user, transmits from said computer to said mobile device of said user said progress message;
   (4) in response to said progress message transmitted to said mobile device, receives at said computer from said mobile device said progress measurement;
   (5) stores at said computer said progress measurement;
   (6) compares said progress measurement to said personalized intermediate milestone to determine if said personalized intermediate milestone has been met;
   (7) generates a reward message to said user if said personalized intermediate milestone has been met, said reward message comprising a redeemable reward consistent with said user's ultimate goal and activity preferences;
   (8) determines a transmission time for said reward message consistent with said user's activity preferences;
   (9) transmits said reward message to said user mobile device at said transmission time.

2. The computerized method of claim 1 wherein said personalized intermediate milestone comprises any one of the following: a loss of a certain amount of body weight, attaining a certain body fat percentage, or achieving a certain waist size.

3. The computerized method of claim 1 wherein the expert system further stores at said computer said reward message and permits said user to view said reward message after it is sent.

4. The computerized method of claim 1 wherein said reward message comprises a coupon to be printed by said user from a personal computer.

5. The computerized method of claim 1 wherein said reward message comprises a check issued to said user.

6. The computerized method of claim 1 wherein said reward message comprises a discount at a meal provider, a fitness center, a clothing store, or a fitness equipment store.

7. The computerized method of claim 1 wherein the expert system further presents stored progress data to said user in a graphical manner.

8. The computerized method of claim 1 further comprising:
(d) accepting in a computer accessible database location data for a plurality of entertainment establishments; and wherein the expert system further
   (1) receives at said computer location data from said user comprising said user's current location;
   (2) compares at said computer said user's current location to location data for at least one of said plurality of entertainment establishments in said computer accessible database; and
   (3) sends from said computer to said user a reward message comprising a redeemable reward for use in an entertainment establishment in proximity to said user's current location.

9. The computerized method of claim 1 wherein the expert system further permits said user to do any one of the following: combine rewards, exchange rewards, or combine and exchange rewards.

10. The computerized method of claim 1 wherein the expert system further sends from said computer a message of encouragement to said mobile device if said user has not responded to said progress message.

11. A computerized system for rewarding a user for accomplishing a personalized intermediate milestone based on an ultimate goal, the system comprising:
   a nutrition provider computer accessible database for storing nutrition data for a plurality of meals offered by a plurality of providers;
   a computer accessible user data database for storing data related to diet and exercise preferences for a plurality of users and goals related to said diet and exercise preferences;
   a server for receiving and storing at said computer accessible user data database user data comprising:
   contact data for a mobile device of said user;
   diet preferences of said user, said diet preferences related to a preferred meal plan, preferred foods, and meal preparation options;
   a goal of said user, comprising one of the following:
       reaching a specific weight;
       reaching a specific body fat percentage;
       maintaining a certain exercise schedule; or
       reaching a specific waist size; and
   a computerized expert system executing at said server for:
   generating at least one personalized intermediate milestone for said user based on said goal of said user, said personalized intermediate milestone:
       different than said goal; and
       consistent with said user's personal data;
   generating meal messages for said user comprising meal suggestions according to said user's preferred meal plan, preferred foods, and meal preparation options;
   generating progress messages for said user comprising requests for a progress measurement from said user;
   generating a time for transmitting each one of said meal messages and progress messages, said time consistent with said user's diet and exercise preferences; and
   a communications network connected to said server for using said contact data from said user and said times to transmit said meal messages to said mobile device of said user, to transmit said progress messages to said mobile device of said user, and to receive a progress measurement from said mobile device of said user comprising any one of the following:
   said user's weight;
   said user's waist size;
   said user's body fat percentage; or
   said user's exercise habits;
   wherein said progress measurement is received from said communications network at said server, said computerized expert system compares said progress measurement with said personalized intermediate milestone, and said computerized expert system generates and sends to said mobile device of said user a reward message comprising a redeemable reward consistent with said user's diet and exercise preferences if said personalized intermediate milestone has been met.

12. The computerized system of claim 11 further comprising:
   a computer accessible provider database comprising location and reward data for a plurality of providers;
   location data from said communications network regarding said user's current location;
   wherein said expert computerized system compares said user's current location to location data for said plurality of providers in said computer accessible database and sends a reward message to mobile device of said user comprising a reward for use at one of said providers in proximity to said user's current location.

13. The computerized system of claim 12 wherein said provider is selected from the group consisting of: restaurants, fitness centers, clothing stores, and fitness equipment stores.

14. The computerized system of claim 12 wherein said progress measurement is stored in said computer accessible user data database and said progress measurement is presented to said user in a graphical manner.

15. The computerized system of claim 12 wherein computerized said expert system sends a message of encouragement to said mobile device said user if said user has not responded to said progress messages.

16. A computerized method for personalizing a reward message from a computerized expert system to modify health behavior comprising:
- (a) prompting from a server a user to provide personal data comprising contact information for a portable device;
- (b) prompting from said server said user to provide preference data comprising preferences for:
  - (1) completing at least one activity related to at least one health behavior; and
  - (2) a preferred time for completing said at least one activity;
- (c) prompting from said server said user to:
  - (1) select from a plurality of behavioral challenges a behavioral challenge identifying a difficulty in changing said at least one health behavior; and
  - (2) select from a plurality of challenge strategies a challenge strategy for overcoming said difficulty;
- (d) saving said user personal data, preference data, and challenge data in a first computer accessible database;
- (e) entering in a second computer accessible database message data related to said at least one health behavior and related to changing said at least one health behavior;
- (f) generating automatically at said server a tailored reward message for said user using said preference data and said challenge data and said message data from said second computer accessible database, said tailored reward message comprising content directed to a reward for overcoming said challenge to changing said at least one behavior;
- (g) determining a transmission time for said tailored reward message consistent with said user's preferred time;
- (h) using said contact information, sending said tailored reward message to said portable device at said transmission time.

17. The computerized method of claim 16 wherein said reward message comprises a coupon to be printed by said user from a personal computer.

18. The computerized method of claim 16 wherein said reward message comprises a check issued to said user.

19. The computerized method of claim 16 wherein said reward message comprises a discount at a meal provider, a fitness center, a clothing store, or a fitness equipment store.

20. The computerized method of claim 16 further comprising:
- (i)) entering in a computer accessible database location data for a plurality of entertainment establishments;
- (j) receiving at said computer location data from said user comprising said user's current location;
- (k) comparing at said computer said user's current location to location data for at least one of said plurality of entertainment establishments in said computer accessible database; and
- (l) sending from said computer a reward message to said user comprising a reward for use in an entertainment establishment in proximity to said user's current location.

* * * * *